United States Patent
Klavetter et al.

(10) Patent No.: US 11,378,547 B1
(45) Date of Patent: Jul. 5, 2022

(54) ELECTROCHEMICAL DETECTION OF GAS PHASE CHEMICALS

(71) Applicant: National Technology & Engineering Solutions of Sandia, LLC, Albuquerque, NM (US)

(72) Inventors: Kyle Chris Klavetter, Albuquerque, NM (US); William G. Yelton, Sandia Park, NM (US); Tina M. Nenoff, Albuquerque, NM (US); Michael P. Siegal, Albuquerque, NM (US); Carlos R. Perez, Albuquerque, NM (US)

(73) Assignee: National Technology & Engineering Solutions of Sandia, LLC, Albuquerque, NM (US)

(*) Notice: Subject to any disclaimer, the term of this patent is extended or adjusted under 35 U.S.C. 154(b) by 421 days.

(21) Appl. No.: 16/572,978

(22) Filed: Sep. 17, 2019

Related U.S. Application Data

(60) Provisional application No. 62/737,446, filed on Sep. 27, 2018.

(51) Int. Cl.
| | | |
|---|---|---|
| *G01N 27/403* | (2006.01) | |
| *G01N 27/49* | (2006.01) | |
| *G01N 27/31* | (2006.01) | |
| *C12M 3/06* | (2006.01) | |
| *G01N 27/30* | (2006.01) | |
| *C25D 11/04* | (2006.01) | |

(52) U.S. Cl.
CPC ............ *G01N 27/49* (2013.01); *C12M 23/16* (2013.01); *C25D 11/045* (2013.01); *G01N 27/301* (2013.01); *G01N 27/304* (2013.01); *G01N 27/31* (2013.01); *G01N 27/403* (2013.01)

(58) Field of Classification Search
CPC ............ G01N 27/404; G01N 27/4071; G01N 27/4045; G01N 27/403
See application file for complete search history.

(56) References Cited

U.S. PATENT DOCUMENTS 7,481,912 B2 * 1/2009 Stelzle ............... G01N 27/3278
                                                    204/403.01
7,625,469 B1    12/2009 Yelton et al.

OTHER PUBLICATIONS

Lee et al., "Low-cost microarray thin-film electrodes with ionic liquid gel-polymer electrolytes for miniaturized oxygen sensing," Analyst, 2016, 141, 3705 (Year: 2016).*

(Continued)

*Primary Examiner* — Alexander S Noguerola
(74) *Attorney, Agent, or Firm* — Martin I. Finston; Mark A. Dodd

(57) ABSTRACT

We provide an electrochemical sensor in which working microelectrodes are arranged in an array and interconnected in parallel. The working electrodes are arranged so that in use, they are electrochemically coupled to a counter electrode structure through an electrolyte. The sensor also includes a microporous body arranged so that in use, it is situated at a boundary between a gaseous environment and the electrolyte. In another aspect, we provide a method of sensing in which a sample of gas is admitted to a liquid electrolyte maintained by pores of a porous substrate. A voltage is applied to the liquid electrolyte, and an electrical response to the applied voltage is observed, thereby to detect electrochemical evidence of an analyte within the liquid electrolyte.

20 Claims, 12 Drawing Sheets

Step 3. Release of iodide from silver by electrochemical reaction.

Step 4. Electrochemical detection of iodide, measured by detection of the electron released during iodide oxidation.

(56) References Cited

OTHER PUBLICATIONS

Lee et al., "Oxygen reduction voltammetry on platinum macrodisk and screen-printed electrodes in ionic liquids: Reaction of the electrogenerated superoxide species with compounds used in the paste of Pt screen-printed electrodes?", Electrochimica Acta 101 (2013) 158-169 (Year: 2013).*

Huang et al., "Toward Membrane-Free Amperometric Gas Sensors: A Microelectrode Array Approach," Anal. Chem. 2010, 82,5238-5245 (Year: 2010).*

Bonhomme, F. et al., "CO2 selectivity and lifetimes of high silica ZSM-5 membranes," Microporous and Mesoporous Materials (2003) 66:181-188.

Chapman, K. W. et al., "Trapping Guests within a Nanoporous Metal-Organic Framework through Pressure-Induced Amorphization," J. Am. Chem. Soc. (2011) 133:18583-18585.

Chemical Reviews, 2012 Metal-Organic Framework Issue, vol. 112:673-1268.

Chemical Society Reviews, 2009 Metal-organic frameworks issue, vol. 38:1213-1504.

Godino, N. et al., "Mass Transport to Nanoelectrode Arrays and Limitations of the Diffusion Domain Approach: Theory and Experiment," J. Phys. Chem. C (2009) 113:11119-11125.

Guerrero, V. V. et al., "HKUST-1 membranes on porous supports using secondary growth," Journal of Materials Chemistry (2010) 20:3938-3943.

Ito, T. et al., "Cyclic voltammetry on recessed nanodisk-array electrodes prepared from track-etched polycarbonate membranes with 10-nm diameter pores," Analyst (2010) 135:172-176.

Klavetter, K. C. et al., "Nanoelectrode arrays for in-situ identification and quantification of halogen ions in water," 232nd ECS Meeting, Symposium M01—Sensors, Actuators and Microsystems General Session, National Harbor, MD, Oct. 1-6, 2017, SAND2017-04041A, 35 pages.

Klavetter, K. C. et al., "In-situ trace-level halide analyte separation and detection using high-aspect ration nano-electrode arrays," Sandia National Laboratories, SAND2017-6444C, 1 pages.

Klavetter, K.C. et al., "Nanoelectrode Arrays for in-situ Identification and Quantification of Iodine Ions," Sandia National Laboratories, SAND2017-12683C, 21 pages.

Limmer, S. J. et al., "Electrochemical Deposition of Gi2(Te,Se)3 Nanowire Arrays on Si," Journal of the Electrochemical Society (2012) 159(4):D235-D239.

Morishige, K. et al., "Kinetics of Capillary Condensation of Water in Mesoporous Carbon: Nucleation and Meniscus Growth," The Journal of Physical Chemistry C (2015) 119:18287-18292.

Nan, J. et al., "Step-by-Step Seeding Procedure for Preparing HKUST-1 Membrane on Porous α-Alumina Support," Langmuir (2011) 27:4309-4312.

Nenoff, T. M. et al., "Membranes for Hydrogen Purification: An Important Step toward a Hydrogen-Based Economy," MRS Bulletin (2006) 31:735-744.

Nenoff, T. M., "MOF membranes put to the test," Nature Chemistry (2015) 7:377-378.

Nenoff, T. M. et al., "Cs+ Removal from Seawater by Commercially Available Molecular Sieves," Solvent Extraction and Ion Exchange (2012) 30:33-40.

Qiu, S. et al., "Metal-organic framework membranes: from synthesis to separation application," Chem. Soc. Rev. (2014) 43:6116-6140.

Rochford, C. et al., "Planarized arrays of aligned, untangled multiwall carbon nanotubes with Ohmic back contacts," J. Mater. Res. (2015) 30(2):315-322.

Sava, D. F. et al., "Competitive I2 Sorption by Cu-BTC from Humid Gas Streams," Chemistry of Materials (2013) 25:2591-2596.

Sava, D. F. et al., "Capture of Volatile Iodine, a Gaseous Fission Product, by Zeolitic Imidazolate Framework-8," J. Am. Chem. Soc. (2011) 133:12398-12401.

Tang, Z. et al., "Internal Surface Modification of MFI-Type Zeolite Membranes for High Selectivity and High Flux for Hydrogen," Langmuir (2009) 25(9):4848-4852.

Yelton, W. G. et al., "Porous Al2O3 Nanogeometry Sensor Films, Growth and Analysis," Journal of the Electrochemical Society (2002) 149(1):H1-H5.

Yelton, W. G. et al., "Functionalized nanoelectrode arrays for in-situ identification and quantification of regulated chemicals in water," Impacts of Global Climate Change: Proceedings of the 2005 World Water and Environmental Resources Congress, 12 pages.

Zhang, Y. et al., "Array of recessed gold nanoelectrodes formed with polymethylmethyacrylate for individual detection of ascorbic acid, dopamine and uric acid," Electrochimica Acta (2016) 212:25-31.

* cited by examiner

Step 3. Release of iodide from silver by electrochemical reaction.

Step 4. Electrochemical detection of iodide, measured by detection of the electron released during iodide oxidation.

ELECTROCHEMICAL DETECTION OF GAS PHASE CHEMICALS

CROSS-REFERENCE TO RELATED APPLICATION

This application claims the benefit of U.S. Provisional Application No. 62/737,446, filed Sep. 27, 2018, under the title "Electrochemical Detection of Gas Phase Chemicals", the entirety of which is hereby incorporated herein by reference.

ACKNOWLEDGEMENT OF GOVERNMENT SUPPORT

This invention was made with United States Government support under Contract No. DE-NA0003525 between National Technology & Engineering Solutions of Sandia, LLC and the United States Department of Energy/National Nuclear Security Administration. The United States Government has certain rights in this invention.

TECHNICAL FIELD

This invention relates to electrochemical detection and analysis using a microelectrode array. In specific embodiments, the invention relates to applications for in-situ analysis of gaseous chemicals in air or other gaseous environments. In specific embodiments, the invention relates to in-situ analysis performed with the assistance of chemically selective preconcentrators.

ART BACKGROUND

Electrochemical analysis is a highly sensitive, chemically selective method for identifying and quantifying many different ionized chemicals in water. Sensitivity levels of 1 ppb or better are achievable for many chemicals, including those regulated by the U.S. Environmental Protection Agency (EPA). However, electrochemical analysis has historically required that field samples be transported back to an analytical laboratory. There, additional laboratory chemicals are typically added to a sample before analysis is performed using bench-scale equipment. Such analysis requires skilled laboratory technicians and causes often undesirable time delays.

We previously developed a microelectrode array technology that helps to overcome these problems. Our microelectrode array technology is described in U.S. Pat. No. 7,625,469, which issued to William G. Yelton et. al. on Dec. 1, 2009 under the title, "Nanoelectrode Array for Electrochemical Analysis," which is commonly owned herewith, and which is hereby incorporated herein by reference in its entirety. U.S. Pat. No. 7,625,469 will hereinafter be referred to as "the '469 patent".

The electrochemical sensor of the '469 patent can be built on a substrate of choice such as silicon, sapphire, alumina, or glass. With available fabrication techniques, the areal density of individual sensor units can reach tens of billions per square centimeter. Scaling the number of sensor units in the microarray provides an additive increase in signal response. As a consequence, this technology offers detection limits on the order of 1 ppb.

The microarrays enable higher sensitivity by providing greater signal response than macroscopic disk electrodes, due to enhanced mass transport from radial diffusion. Appropriate material selection for the working and counter electrodes offers an initial degree of analyte selectivity through control of the applied voltage. By combining multiple microelectrode arrays having different working electrode materials, the sensor can be designed to have unique fingerprint responses to target species and to suppress false-positive responses to similar chemical species.

Due to the microscale geometry of the sensor, low microampere operating powers are sufficient for data storage and monitoring. Because of its high redundancy, the microelectrode array is robust against sensor fouling.

There is still a need for new approaches to electrochemical sensing that increase sensitivity while minimizing false positive responses. In particular, there is a need for new approaches that are both more sensitive and more selective for target analytes.

There is also a need for new sensing techniques that can be practiced from relatively great distances where analyte concentrations are low out of concern, for example, for personnel safety. One approach that addresses this need extends electrochemical detection technology to gas-phase chemical species, for example to remotely detect gas-phase contaminants emitted from hazardous manufacturing activities or geological events. Providing real-time detection and analysis of such gas species could greatly benefit the health and security of the general population, improve the safety of first responders, and enhance the monitoring of manufacturing processes.

SUMMARY OF THE INVENTION

We have developed a new microelectrode array sensor concept. According to various embodiments, the sensor includes an array of working microelectrodes referred to here as the "MEA", and it includes one or more electrodes to perform the functions of auxiliary and reference electrodes. (In some embodiments, as explained below, a single electrode can perform both the auxiliary and reference functions.) The sensor also includes a microporous material that, in operation, maintains a liquid environment between the working electrode and the electrode or electrodes serving as the auxiliary and reference electrodes.

For purposes of the present discussion, the working electrode is the electrode at which an electrochemical reaction is driven by applied voltage and a current signal is measured. To maintain ionic balance in the electrochemical cell, the auxiliary electrode generates a current equal in magnitude of current but opposite in sign to the current generated at the working electrode. The reference electrode is the electrode against which the working electrode potential is measured. As noted, the reference electrode may be the same electrode as the auxiliary electrode in some circumstances.

For purposes of the present discussion, microscale structures are structures having at least one significant dimension, such as diameter, that is 10 µm or less. This definition includes within its scope nanoscale structures, which are here defined as having at least one significant dimension that is 100 nm or less. Accordingly, we would regard an electrode as a microelectrode if it has a diameter or mean diameter that is 10 µm or less, and as a nanoelectrode if its diameter or mean diameter is 100 nm or less. Similarly, we would regard a material as microporous if it is permeated with pores having an average diameter of 10 µm or less, and as nanoporous if the average pore diameter is 100 nm or less.

The prefix micro or the prefix nano as used below in terms such as "micropore", "microchannel", "microwell", etc., thus signifies that the structure being referred to is a microscale or nanoscale structure, as appropriate. As explained above, nanostructures are to be understood as a subspecies of microstructures.

In specific embodiments, each working microelectrode is a recessed electrode built into an individual microwell. The microwells can be filled with an aqueous electrolyte such as water or a buffer solution of specified pH, or even a nonaqueous electrolyte such as an organic solvent or ionic liquid. Because of the microdimensionality, the microwells can extract sufficient moisture for operation from the environment via capillary condensation, even in low-humidity, desert-like climates. The microgeometry also inhibits the electrolyte from escaping the microwells by evaporation, making it possible for the electrolyte to subsist for the electrochemical detection of captured and dissolved atmospheric gases.

For at least some applications, the electrolyte can be selected specifically for the analyte that is to be detected. For example, an aqueous electrolyte may be chosen for capturing halogen gases from the atmosphere. Halogen gases will dissolve in aqueous solutions and hydrolyze into ionic species that may be detected by their electrochemical reduction or oxidation at the working electrode.

In other embodiments, the working microelectrodes are not recessed, but instead are coplanar, i.e., they terminate at ends (by an adopted convention, we refer to these ends, without loss of generality, as "top" ends) that are flush with a substrate surface that contacts the electrolyte. In yet other embodiments, the working microelectrodes are prominent, that is, they are raised above the substrate surface that contacts the electrolyte.

Accordingly, recessed microelectrodes may be formed directly within the pores of the microporous material (in which case each pore constitutes a microwell), or in other embodiments an array of coplanar or prominent working microelectrodes may be used. In either case, a microporous material in some form is provided for maintaining the adjacent liquid environment.

In further developments, we add a metal film that can selectively capture and preconcentrate a dissolved or hydrolyzed analyte (or more than one such analyte) that serves as a marker species for the gas targeted for detection. Such a film may be within the pores of the microporous material, or in any other location that permits it to be in contact with the electrolyte. The capture mechanism is controlled by applying a voltage to the metal film. The voltage is chosen to drive a desired electrochemical reaction between the film and the marker species. The reaction produces a solid phase that retains the marker species (with or without application of voltage, depending on the specific embodiment) until it is released for detection by applying a voltage sufficient to drive the reverse electrochemical reaction.

In further developments, we add a bed of preconcentrator material that can selectively preconcentrate a target gas by adsorption over a period of time from the ambient atmosphere and can then release the gas on command into the microelectrode array for sensing. Suitable preconcentrator materials include zeolites, metal-organic framework (MOF) materials, and activated carbons. The controlled release process may be driven, for example, by temperature, pressure, or electrochemical potential.

Preconcentration can increase sensitivity by integrating the collection of the target species over time. Tailoring the preconcentrator material to the target analyte can reduce false positive detections by making the collection more chemically selective.

DETAILED DESCRIPTION

Figure 1:
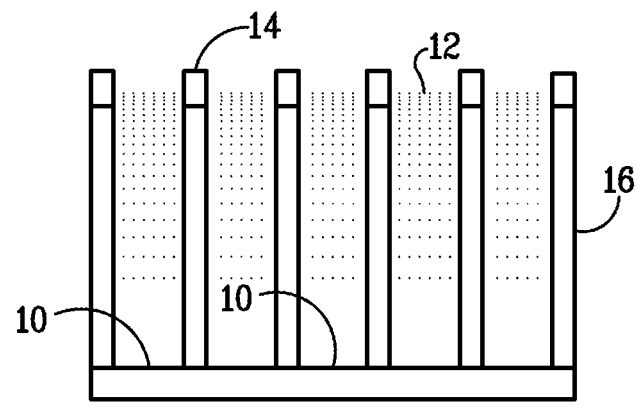
FIG. 1 is a schematic drawing of an example microelectrode array in which the working microelectrodes are recessed according to principles described hereinbelow.

In embodiments of the invention, a template is provided as the structural foundation of the sensor. The template is an electrically insulating substrate, typically slab-like, in which there is defined a microporous array. One example is provided by the nanoelectrode array (NEA) of the '469 patent. However, it should be understood that various alternative types of microporous arrays would be suitable as templates, and thus the scope of the present invention should not be deemed to be limited by the particular embodiments that are described here.

In that regard, we believe that any material with regular channels could be a potential template. Examples include anodized aluminum oxide (AAO; discussed below), anodized titanium oxide, track etched membranes, and templated microporous oxides.

It should be noted that suitable microelectrode arrays can also be made by techniques that do not involve microporous templates. For example, microelectrode arrays can be fabricated lithographically. In other examples, plasma vapor deposition (PVD) can be used to create microcolumnar arrays.

Turning back to embodiments in which a template constitutes the structural foundation, we note that in a suitable template, the bottoms of all the channels should be in parallel electrical contact with each another, and there should be a backside electrical contact, enabling the pore bottoms to act as the working electrodes of the sensor array.

For particular applications, a channel material may be required that is chemically stable when contacted by a required electrolyte. (For example, alumina is stable over the range from pH2 to pH12, but only when in the alpha phase. By contrast, alumina in the amorphous boehmite phase is stable only from pH5 to pH8). The channel dimensions may also be critical for certain applications, because the rate of capillary condensation depends on the channel diameter, as well as the temperature and relative humidity. Hence, a sensor designed to maintain a constant liquid volume in a specified temperature and humidity regime may need specially tailored channel dimensions.

By way of example, channel diameters in the range 20-100 nm will be suitable for many applications, but those dimensions should not be regarded as limiting.

The nanoelectrode array (NEA) of the '469 patent includes an electrically conducting substrate, an insulating layer on the substrate, and a plurality of hollow pores formed through the insulating layer to provide a plurality of working nanoelectrodes.

Example arrays of the '469 patent is fabricated by lithographic patterning. Through lithographic patterning, the array can be designed in a grid, e.g. a rectangular or hexagonal grid, with a uniform electrode spacing. However, it is not critical for the array to have a uniformly periodic electrode spacing. Hence other methods to form a micropore template can also be used and may be more desirable in some cases. For example, we will describe, below, an alternative type of array made from anodized aluminum oxide (AAO).

For templates in which the microelectrode array is recessed, with each electrode deposited within one of the micropores, a conducting layer is deposited on the top surface of the insulating layer. The purpose of this layer is to provide a counter electrode, which will typically serve the functions of both an auxiliary and a reference electrode. In particular embodiments, the working microelectrodes can be functionalized to provide selectivity for a specific analyte.

For lithographic patterning as described, e.g., in the '469 patent, a resist layer is advantageously patterned by directed beam or projection methods. For example, electron-beam lithography can form micropores in a resist-coated substrate by direct writing. An inexpensive positive resist that has good sensitivity, tone, resolution, and etching resistance, such as polymethyl methacrylate (PMMA), can be used as the template film. Because the electron beam can have a large depth of focus, high-aspect-ratio cylindrical pores with uniform diameters can be formed through the resist layer.

Importantly, the pore radius can be as large as 1 μm or more and as small as 100 nm or less when written with a high-energy electron beam, because optical diffraction limits are not applicable. Instead, there is a resolution limit of about 10 nm due to solid-state electron scattering. Other lithographic methods capable of microscale resolution, such as extreme ultraviolet, X-ray, or ion-beam lithography may also be useful in this regard.

In alternative approaches, a micropore template is fabricated by electrochemically anodizing a metal. The metal workpiece can be either freestanding (in the form, for example, of a foil or sheet) or deposited as a layer on a substrate-of-choice (SoC). Suitable SoC materials include silicon, sapphire, glass, and any of various other materials that will withstand the electrochemical anodization environment. In this regard, useful reference is made to the '469 patent, cited above, and to the article W. G. Yelton et al., "Porous $Al_2O_3$ Nanogeometry Sensor Films: Growth and Analysis," *J. Electrochem. Soc.* 149(1) (2002) H1-H5.

For the metal workpiece, aluminum is a good candidate material. Alternatives include silicon and titanium, among other materials.

The anodization of aluminum, for example, transforms it into anodized aluminum oxide (AAO). As is well known in the art, suitable anodization conditions will create an AAO layer with a quasi-hexagonal array of close-packed pores aligned vertically and extending through the thickness of the AAO. Pore diameters are controllable over a range from less than 5 nm to greater than 300 nm. For example, an illustrative layer of AAO used to measure iodine gas has 120-nm pores regularly spaced with a pore periodicity of 280 nm and a pore density of $1.5 \times 10^9$ pores/$cm^2$.

The oxidative process driven by anodization will initially nucleate on the metal surface and will propagate as a reaction front through the thickness of the material until the backside of the workpiece is reached or until the process is actively terminated. Termination of either kind will leave behind a solid plug of metal oxide in each pore at the backside of the array (and thus in the bottom of each pore). In an AAO array, these are insulating plugs of aluminum oxide.

As explained above, the '469 patent provides an example in which the array of hollow pores is formed in an insulating layer affixed to an electrically conductive substrate. Each pore terminates, at bottom, at the surface of the electrically conductive substrate. Thus, the electrically conductive substrate can itself provide the working electrode, or alternatively, a working electrode can be grown within each pore. For example, an electrodeposited working electrode can be grown upward from the electrically conductive substrate. This can be done using AAO micropore templates as well.

Irrespective of the type of micropore template, it is important that the working microelectrodes be electrically interconnected and able to operate in parallel via a backside contact of some kind. The front sides of the working microelectrodes within the array should be distinct, somewhat regularly spaced, somewhat regularly sized, and electrically isolated from the micropore template surface. The working microelectrodes can be located below, at, or above the micropore template surface, depending on device design.

In embodiments in which the working microelectrodes are at or near the micropore template surface, maintaining a distinct separation between electrodes is advantageous because of mass transport effects in the electrolyte. As is known in the art, the ionic flux profile of extended planar electrodes is predominantly directed along a normal to the electrode surface, whereas the flux profile of an isolated point-like electrode set in a planar surface is largely radial over a solid angle approaching a hemisphere. The radial geometry has the potential to support a greater flux of analyte. As a consequence, replacing a single continuous electrode with a multiplicity of small, separated electrodes can lead to higher current signals (at a given voltage). Due to the smaller electrode surface area, it can also lead to lower ohmic (i.e., IR) drops between the detecting and auxiliary/pseudoreference electrodes.

For the sensor to operate, a liquid phase must be present in an amount sufficient to maintain ionic conductivity between the working microelectrodes and the electrode(s) used to complete the electrochemical cell. (If the auxiliary and reference electrodes coincide, the electrochemical cell can operate with, effectively, only two electrodes.) A microporous material is needed between the aforementioned liquid phase and the gas phase, or atmosphere, to which the sensor is exposed. The primary purpose of this microporous material is to maintain the liquid phase and suppress its evaporation, via capillary condensation.

Below, we provide three different example designs for the device that can be constructed according to the principles stated above.

The first and simplest example, illustrated schematically in FIG. 1, is an MEA comprising recessed working microelectrodes 10, in which the working microelectrodes are recessed relative to the top of the microporous material. Here, the micropores define the working microelectrode dimensions. Liquid 12 is contained within each micropore, which consequently functions as a distinct electrochemical cell. The liquid provides ionic conduction between the MEA and the auxillary/reference electrode 14, which in this design is constituted by a metal deposited onto the top surface (i.e., the surface opposite to the substrate) of the AAO or other microporous material 16.

Figure 2:
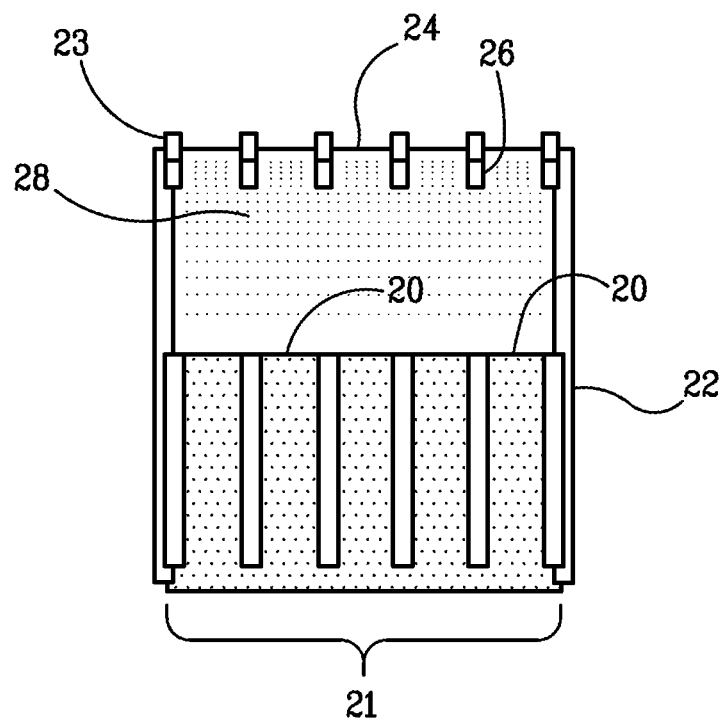
FIG. 2 is a schematic drawing of an example microelectrode array in which the working microelectrodes are coplanar according to principles described hereinbelow.

The second example, illustrated in FIG. 2, is an MEA 21 constituted by coplanar working microelectrodes 20, in which the working microelectrodes are coplanar with the top of the microporous material 22. A second body 23 of microporous material may be provided to help maintain the liquid/gas boundary 24 and to serve as a platform upon which the auxillary/reference electrode 26 is located. In this concept, the liquid phase 28 is located between the MEA 21 and the microporous material 23, which in some non-limiting examples may be AAO.

Figure 3:
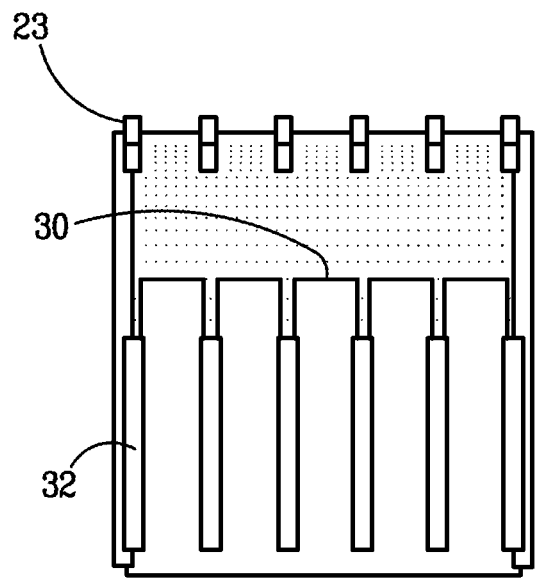
FIG. 3 is a schematic drawing of an example microelectrode array in which the working microelectrodes are prominent according to principles described hereinbelow.

The third example, illustrated in FIG. 3, is an MEA constituted by prominent working microelectrodes 30, in which the working microelectrodes are prominent above the top of the microporous material 32. This is very similar to the second example, except that here, the electrodes grow beyond the top surface of the micropore template surface. Possible examples of suitable prominent structures include carbon microtubes grown via chemical vapor deposition, and conductive metal electrodes whose end portions are exposed by a preferential chemical etch-back of the micropore template material.

Processing of an AAO Template.

As pointed out above, AAO is a useful material from which to fabricate an MEA, but it is not the only such material. Below, we will present several different example processes for making a sensor with an AAO micropore template. Depending on the specific design, the AAO component may be freestanding, or it may be affixed to a substrate.

To process a freestanding AAO micropore template, the metal-oxide plug is removed from the bottoms of the pores, and then the working electrode material is deposited into the pore bottoms. Several different methods may be suitable for removing the metal oxide, including without limitation chemical etching, mechanical polishing, and ion-beam milling. Exemplarily, the working electrode material can be added by simply coating it onto the bottom AAO surface in a thickness sufficient to completely close off the mouths of the micropores. In a more complex process, a base layer of a first electrically conductive material is added as above, and then to form the working electrodes, the micropores are partially filled with a second conductive material that is deposited electrochemically on the first material.

With either approach, the conducting layer used to coat the AAO pore bottoms should be a good conductor, and it should adhere well to the AAO or other material of the micropore walls. If it is a base layer for deposition of the working electrode in a two-layer process, there should be good electrical contact between the base layer and the working microelectrode material exposed within the micropores.

In order for the resulting device to operate as an electrochemical sensor, electrode reactions should be confined to the interface between the metal working microelectrode and the liquid electrolyte phase. Hence the outer surface of the conducting material (i.e. the surface at the bottom of the array, distal the pores) needs to be isolated from the electrolyte environment. One way to achieve this is to deposit an electrical insulator over the conducting layer on the backside of the array. Thus, for an MEA with recessed working microelectrodes, for example, the working microelectrodes will be exposed to the electrolyte sensing environment only from within the micropores.

Additional factors come into play for a micropore template that is to be grown on a substrate-of-choice (SoC). In the first instance, the substrate material or materials must be electrochemically compatible with the process for anodization. Moreover, the metal-oxide plug formed in the anodization process must be removable despite the fact that it is now underlain by the SoC. We solve this problem by depositing an additional layer, referred to as the "valve layer", onto the SoC before depositing the anodization material (i.e., the material that will be anodized to form the array of micropores).

Typically, the metal-oxide plug is approximately the same thickness as the pore walls. Consequently, straightforward efforts to remove it with a chemical etch will also eat away the pore walls, thus disrupting the entire micropore template. An ideal valve layer would solve this problem by forming, during the anodization process, a surface oxide that can be selectively removed (e.g., by chemical or electrochemical etching) without removing underlying metal and without removing the metal-oxide microarray material produced by the anodization.

For example, tungsten makes a good valve layer for an AAO array. The tungsten valve layer will anodize under the same conditions as the aluminum anodization. When the propagating anodization front reaches the tungsten valve layer, it does not stop, but instead continues to propagate into the tungsten. However, the tungsten oxidizes without forming a micropore. Because the anodization process continues from the aluminum into the tungsten, the reaction removes the aluminum oxide that would otherwise form plugs at the bottoms of the pores. Consequently, the pores are terminated by a layer of tungsten oxide.

The oxidation of tungsten proceeds much more slowly than the anodization of aluminum. As a consequence, the process can be stopped at a point when only a thin upper portion of the valve layer has been oxidized, leaving conductive tungsten metal beneath it. Suitable chemical etchants are available for removing the tungsten oxide from the bottoms of the pores without damage to the AAO template or to the underlying tungsten metal. One such etchant is pH 7 phosphate buffer solution.

The chemical etching of the tungsten oxide exposes the electrically conductive tungsten metal layer at the bottom of the pores, thus providing a base layer for the electrodeposition of a working electrode material for the sensor.

For both a freestanding template and a template on an SoC, there are two further steps that may be carried out in order to make a completed working microelectrode array. In the first of these steps, the working electrode material is electrodeposited into the micropores. This step may be omitted if the workpiece is freestanding and the working electrode material has already been deposited onto the backside of the template. Even in that case, however, it could be desirable to partially fill the micropores with electrodeposited working electrode material to shorten the depth of the micropores.

In the second step, the counter electrode material is deposited onto the top (or front) surface of the micropore template. After the second step, the resulting working microelectrode array will include the following elements in sequence from bottom to top (or in other words, from back to front):

A backside electrical contact;

a working electrode at the bottom of each micropore and parallel-connected through the backside electrical contact to the working electrodes at the bottoms of the other micropores;

the array of micropores, having a thickness (or height) in the range from tenths of a micrometer to hundreds of micrometers; and a topside electrical contact that performs as the counter electrode for the sensor.

In each pore, a void extending above the respective working electrode constitutes the microwell that we discuss below in regard to sensor operation.

Figure 4:
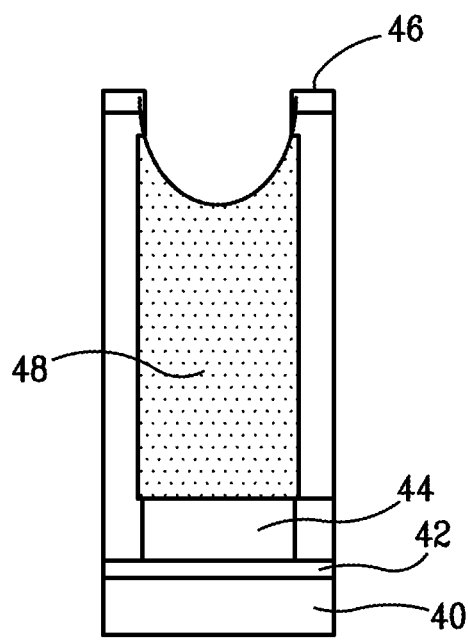
FIG. 4 is a schematic diagram of an individual microwell within a microelectrode array (MEA) according to principles of the invention described here.

A schematic for an individual microwell is shown in FIG. 4. As shown in the figure, the example microwell includes a sapphire substrate 40, a tungsten valve layer 42, a rhodium working electrode 44, and a platinum counter electrode 46. As shown, the microwell is filled with electrolyte 48.

Example 1: Demonstration of Microwell Condensation

The working microelectrode array (i.e., the MEA) will typically be operated using an aqueous electrolyte, although the use of other electrolytes is not excluded and is within the range of uses that are contemplated. The microwells of the MEA may filled with electrolyte by immersion or, at least on the case of aqueous electrolyte, by capillary condensation of atmospheric moisture.

We performed an experimental study to determine the stability of an aqueous fill as a function of relative humidity and temperature. This is an important consideration if, for example, the MEA will be required to operate continuously over a long time interval, especially if the operation is unattended.

An MEA was fabricated using AAO about 50 μm thick with 120-nm-diameter pores. Working electrodes of gold were deposited by physical vapor deposition on the back surface of the template to a thickness sufficient to fully block the micropores. A platinum counter electrode was deposited on the front surface of the template without blocking the pores.

For the physical vapor deposition process, suitable methods include RF sputtering and e-beam evaporation, among others. It should be noted that any of various materials may be used for the working and counter electrodes. Particular material choices may be made according to what specific chemical analyte is to be detected.

The MEA was incorporated in a sensor of the kind depicted in FIG. 1. As noted, the pore diameter was 120 nm.

We tested the sensor functionality in variable relative humidity environments. The ionic conductivity between the working and auxiliary/reference electrodes was measured by impedance spectroscopy to quantify the degree of liquid retention in the pores. The measured results are displayed as a bar chart in FIG. 5.

The sensor was observed to rapidly equilibrate to an absolute impedance value of less than 40 kΩ for relative humidity environments of greater than 33% at a temperature of 50° C. At a relative humidity of 10%, however, the absolute impedance did not equilibrate. Instead, it continuously increased as a function of time, indicating the continuous drying of pores.

More specifically, we observed that the sensor impedance after 6 hours of exposure to 10% relative humidity was approximately equivalent to the equilibrated sensor impedance at 33% relative humidity. However, as indicated in the figure, the sensor impedance was substantially higher after 20 hours at 10% relative humidity. We interpret this as an indication that a significant fraction of the pores in the sensor had dried sufficiently to block, or at least to significantly impede, the ionic conductivity between the working and auxiliary/reference electrodes.

Figure 5:
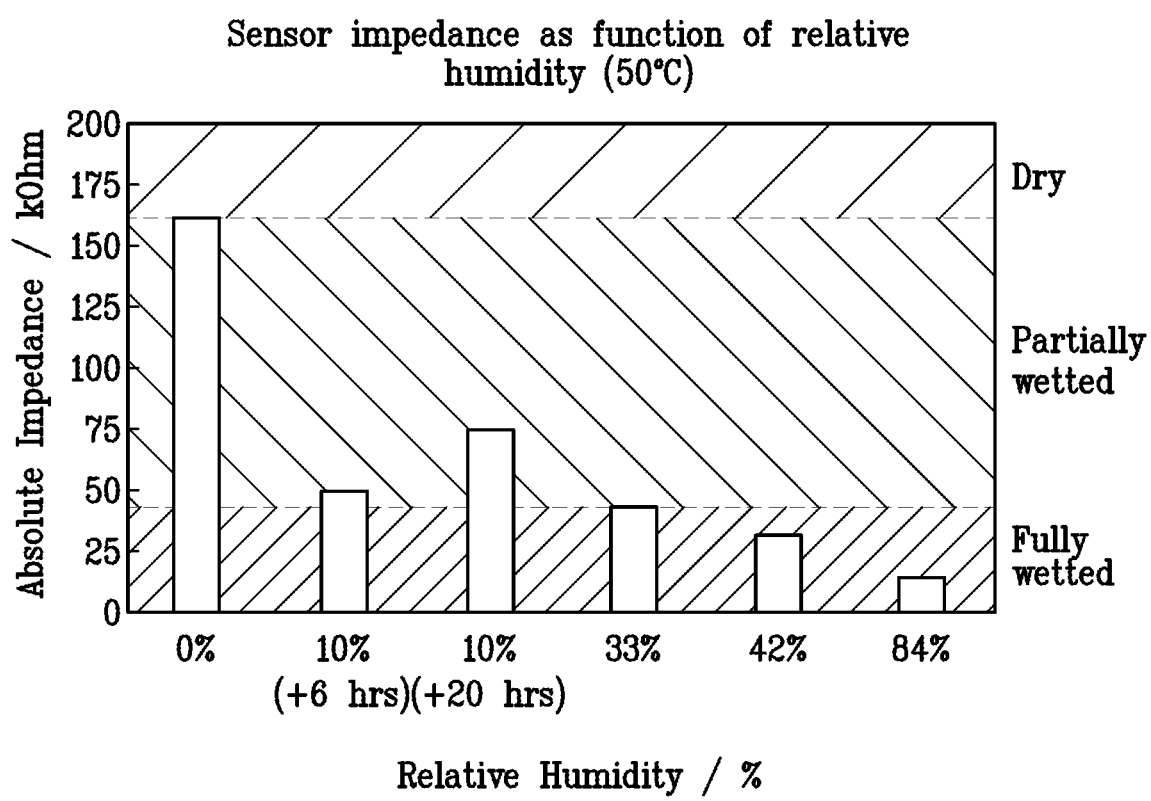
FIG. 5 is a bar chart showing measurements, taken at different relative humidities, of sensor functionality as represented by the ionic conductivity between the working and auxiliary/reference electrodes as measured by impedance spectroscopy. These results help to quantify the degree of liquid retention in the pores.

FIG. 5 demonstrates that there is enough capillary condensation for the MEA to be useful in gas-phase detection. The pores naturally fill with water from the condensation of natural humidity into the micropores, thereby making an electrical connection between the working and counter electrodes.

In use, the MEA can be used to detect any of various analyte gases. Generally, the gases are indirectly sensed after they dissolve in the pore electrolyte solution to form electrochemically detectable species. For some analyte detections, the electrolyte can simply be the condensed water vapor without the need for a supporting electrolyte. However, for detecting some analyte gases, it is advantageous to use an electrolyte solution that has been buffered to fix the pH at a desired level. The capillary condensation can enable the MEA to maintain a pre-fill of such an electrolyte solution if the ambient temperature and humidity fall within a suitable range.

That is, we believe that the rate of evaporation from microchannels (such as the micropores in exemplary embodiments as described here) will be a function of the pore diameter (or other similar microchannel dimensions) at a given value of the relative humidity, just as the rate of capillary condensation into microchannels is a function of microchannel dimension for a given relative humidity. In order to maintain liquid in the reservoir, the rate of evaporation must not exceed that of capillary condensation. We believe that the smaller the micropore diameter, the lower will be the relative humidity at which the liquid level can be maintained.

In this regard, we believe that micropores with very small diameters, for example diameters of about 20 nm, will be especially advantageous. We believe that at such small dimensions, the micropores will be especially effective not only at wicking moisture from the atmosphere, but also at suppressing the evaporative loss of electrolyte, even of pre-loaded electrolyte.

Example 2: Iodine Detection by Gas-Phase Dissolution into the Microwells

We fabricated a prototype MEA for detecting iodine. The MEA was fabricated using a 13 mm diameter, 50-μm thick freestanding micropore template with 120-nm-diameter pores. Working electrodes of gold were deposited on the back surface of the template to a thickness sufficient to fully block the micropores. A platinum counter electrode was deposited on the front surface of the template without blocking the pores.

Figure 6:
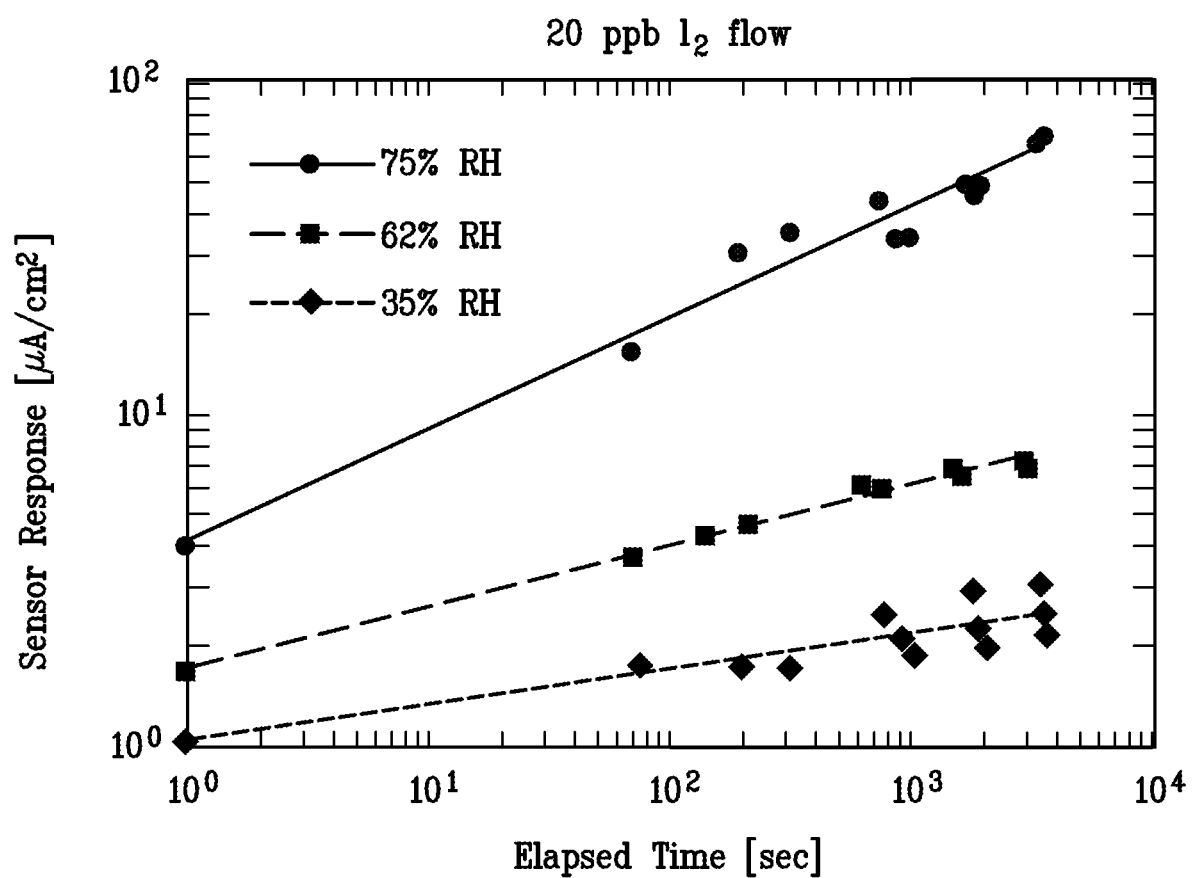
FIG. 6 shows results of an experiment in which cyclic voltammograms were taken from an example MEA before and after exposure to iodine gas at a concentration of about 20 ppb $I_2$ gas in nitrogen. A detection signal recorded at a characteristic voltage for iodine detection is plotted versus time for each of three values of the relative humidity.

We performed an experiment to evaluate how well this design could detect an iodine gas concentration of about 20 ppb in a flow of nitrogen gas moisturized to variable relative humidities, respectively 75%, 62%, and 35%. We performed cyclic voltammetry before and after the iodine gas was introduced into the sensor environment. The signal was recorded at a characteristic voltage suited for detection of iodine gas by the oxidization of its hydrolyzed species The result is shown in FIG. 6.

It is shown that within 100 seconds of exposure to the 20 ppb iodine gas flow, the sensor detected the iodine gas at a response that was ~1×, ~2× and ~10× the baseline current for respective conditions of relative humidity of 35%, 62% and 75%. After 1000 seconds of exposure to the 20 ppb iodine gas flow, the sensor detected the iodine gas at a response that was ~1×, ~2× and ~30× the baseline current for the respective conditions of relative humidity of 35%, 62% and 75%.

Example 3: Detection of Iodide (I$^-$) Anions in Water

We used a prototype MEA of the same design as above to evaluate our ability to detect aqueous iodide at the ppb level. A solution of I$^-$ anions at a concentration of 1 ppb was prepared by dissolving potassium iodide salt in water. The MEA was exposed to the analyte solution by immersion.

The sensor was used in cyclic voltammetry by sweeping the potential from −0.2 to 1.2V relative to a platinum pseudoreference at a sweep rate of 20 mV/s.

Figure 7:
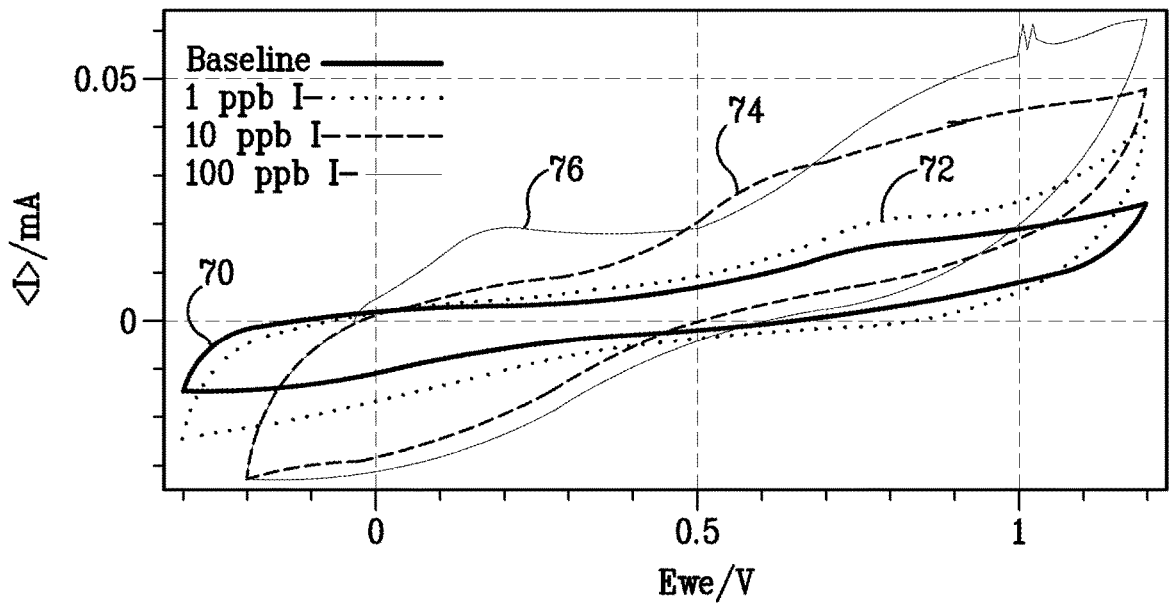
FIG. 7 shows results of an experiment in which cyclic voltammetry was used to detect aqueous iodine. The cyclic voltammograms are displayed for a background sweep conducted for a solution of pH 9 phosphate buffer with no iodide added, and for solutions containing three different concentrations of iodide in water.

FIG. 7 shows the resulting cyclic voltammograms for a background sweep conducted on a solution of pH 9 phosphate buffer with no iodide added (curve 70), and on solutions containing variable concentrations of iodide in water, respectively 1 ppb (curve 72), 10 ppb (curve 74) and 100 ppb (curve 76). The 1-ppb curve exhibits an increase in current at about 0.8 V, which we attribute to the oxidation of the iodide. It is clear from the figure that an iodide concentration as low as 1 ppb is readily resolved above the baseline provided by the background sample.

Figure 8:
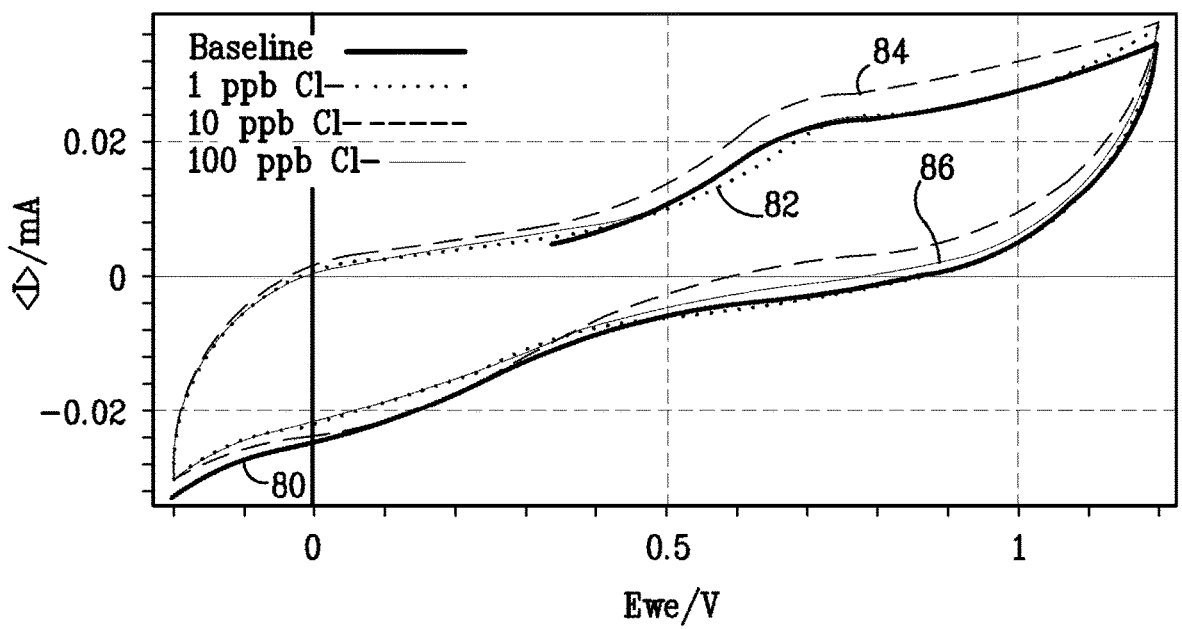
FIG. 8 shows results of an experiment in which cyclic voltammetry was used to detect aqueous chloride. The cyclic voltammograms are displayed for a background sweep conducted for a solution of pH 9 phosphate buffer with no chloride added, and for solutions containing three different concentrations of chloride in water.

Further, FIG. 8 shows cyclic voltammetry for a background sweep conducted on a background solution of pH 9 phosphate buffer with no chloride or iodide added (Curve 80), and on solutions containing variable concentrations of chloride in water, respectively 1 ppb (curve 82), 10 ppb (curve 84) and 100 ppb (curve 86). Notably, no chloride signal is detected in the voltage window (−0.1 to 1.2 V vs the platinum pseudoreference electrode) that was used to clearly detect iodide. The significance of this measurement is that it shows that this sensor can selectively detect iodide vs chloride.

Figure 9:
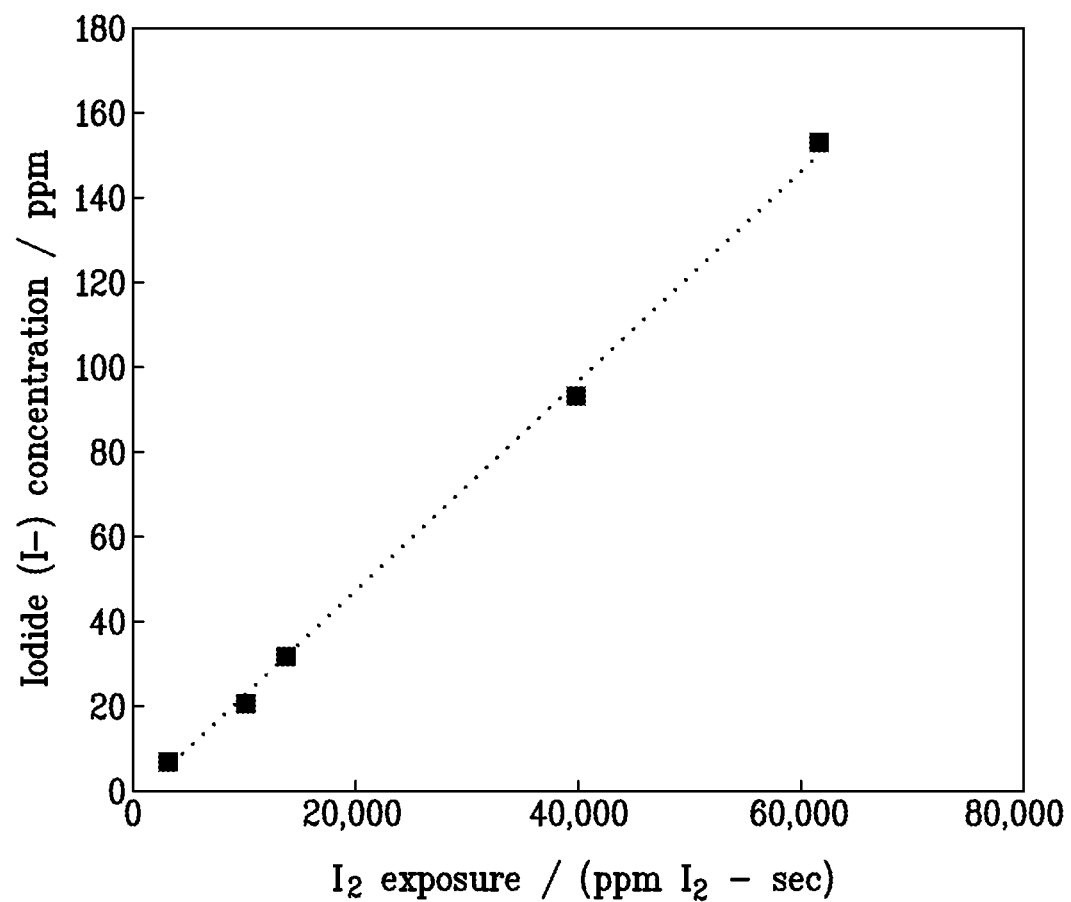
FIG. 9 is a graph illustrating the accumulation of iodide resulting from the hydrolysis of iodine gas in the aqueous electrolyte of a sensor of the kind described here. In the figure, iodide concentration is plotted as a function of iodine gas exposure. As "exposure" in this context is the product of concentration times time, the units on the horizontal axis are ppm-seconds.

It should be noted in this regard that iodide can be accumulated by the hydrolysis of iodine gas in the aqueous electrolyte of the sensor. FIG. 9, which is discussed in greater detail below, shows that flowing iodine gas through a pH 9 buffer solution causes an accumulation of iodide ions in the buffered solution that grows linearly as a function of the production of exposure time and the concentration of iodine in the gas flow.

Further Embodiments 1: Use of Electrochemically Selective Preconcentrator Materials The performance of the electrochemical sensor can be enhanced by incorporating a material that preconcentrates the analyte or an analyte precursor. (An example precursor is iodine gas, which can be preconcentrated for a sensor designed to detect iodide.) The preconcentrator acts in series with the sensor detector. That is, it accumulates the analyte and then in response to an intentional stimulus it releases the analyte into the electrochemical cell. This enables detection at a higher concentration than would otherwise be possible, thus yielding a stronger detection signal.

The preconcentrator may be designed to selectively accumulate the analyte, so that undesired contaminant species are exposed to the sensor detector only in limited or negligible quantities.

Two general categories of preconcentrator material are considered here. Both categories may include chemically selective materials as well as materials that are not chemically selective. The categories are: (1) Materials that operate in a liquid environment, accumulating and releasing analytes in their ionic form; and (2) materials that operate in a gaseous environment, accumulating and releasing analytes (or analyte precursors) in their gaseous form. Each of the two categories encompasses multiple morphologies, including thin films, particles, and porous films, that may be suitable. There are various mechanisms by which the analyte may be accumulated and released from the precursor, including chemical, electrochemical, thermal, and pressure-driven mechanisms.

An example preconcentrator designed to operate in a liquid environment would be provided by a metal that can be reacted with the analyte by an electrochemical oxidation or reduction reaction, thereby accumulating the analyte. For example, silver can serve as the preconcentrator material in an aqueous environment in which iodide is the analyte. Upon application of a sufficiently electrochemically positive bias to the silver, the iodide and silver will electrochemically react to form silver iodide according to:

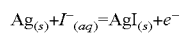

$$Ag_{(s)} + I^-_{(aq)} = AgI_{(s)} + e^-$$

The iodide remains chemically bound to the silver until a sufficiently electrochemically negative bias is applied to the silver iodide, enabling the removal of iodide from the AgI according to the same electrochemical reaction. This simple mechanism to accumulate iodide in silver illustrates not merely preconcentration per se, but rather preconcentration that is controlled and chemically selective.

This electrochemical mechanism enables the preconcentration to be controlled by limiting the amount of charge transferred during the iodide accumulation or release stages, as one electron is transferred per electrochemical reaction of iodide. Hence, the electrochemical mechanism provides a degree of selectivity for the preconcentration of iodide because its accumulation and release are achieved at a specific electrical potential, equivalent to the Gibbs free energy of formation for the reaction. This electrical potential is, for example, hundreds of millivolts lower than what is required for accumulating and releasing a similar species, chloride, from silver. Thus, the method is selective, at least relative to chloride, for the accumulation and release of iodide.

We will now describe an illustrative example of a four-step operator-assisted process using silver as the preconcentrator.

Step 1: A silver electrode is operated in the above-described iodide accumulation mode, in an aqueous solution. The aqueous solution contains some iodide resulting from the hydrolysis of iodine gas.

Step 2: The silver electrode is removed from the aqueous solution and rinsed to remove residual solution.

Step 3: The silver electrode is set into an aqueous volume containing the electrochemical detector cell (including the working microelectrode array), and it is operated in the above-described iodide release mode.

Step 4: The working microelectrode array detector is used to measure the concentration of the released iodide.

Figure 10:
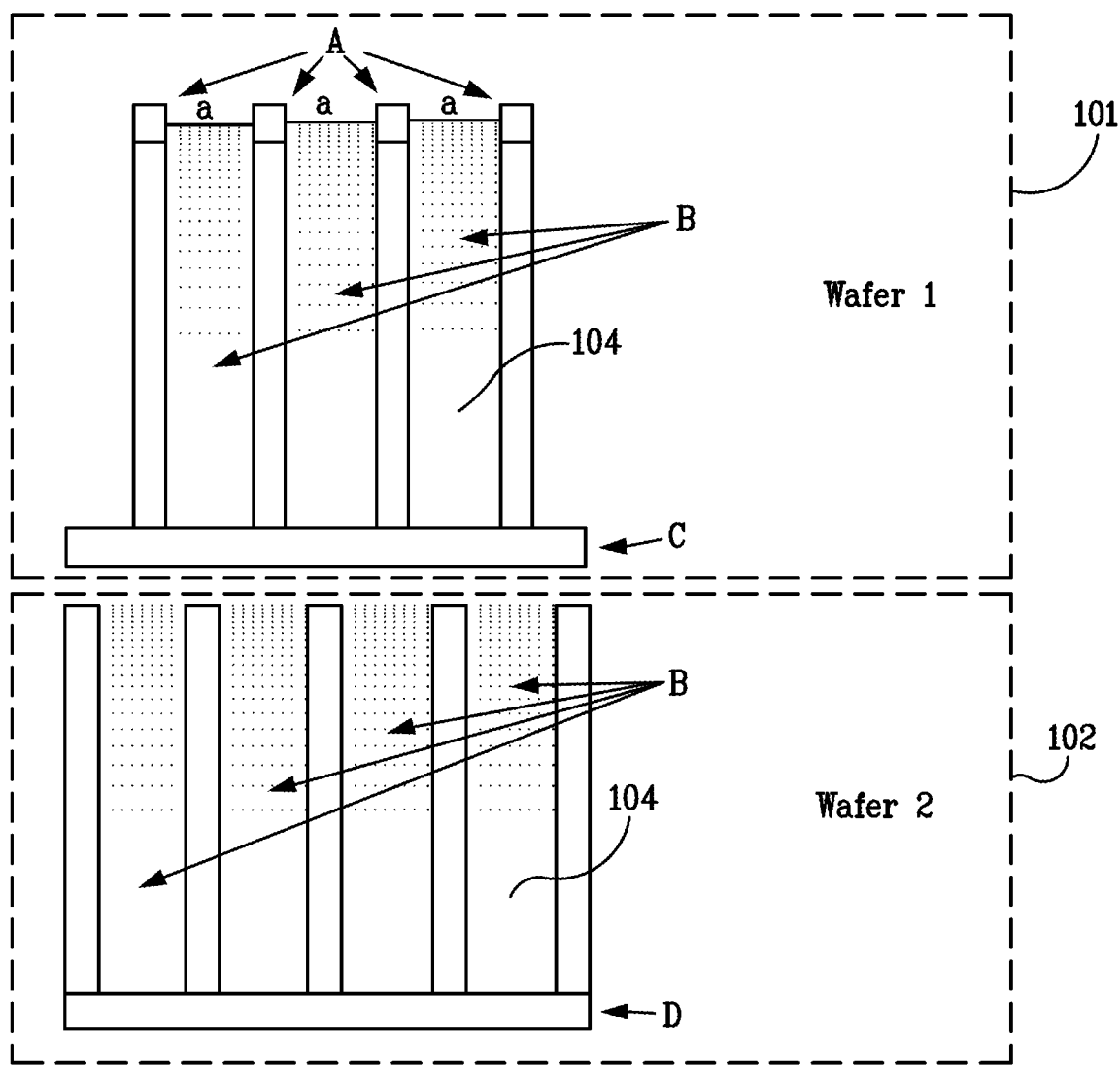
FIG. 10 is a schematic drawing of a sensor in which a silver electrode is used as a preconcentrator for detection of, e.g., iodide.

We will now provide an illustrative example of iodide detection by an autonomous sensor using a silver electrode as a preconcentrator. FIG. 10 depicts a sensor consisting of two metallized AAO wafers 101, 102 stacked on top of one another and filled with an aqueous phase B that fills the lower wafer 102 and the space between wafer 102 and the upper wafer 101.

It is not critical for the microchannels 104 in the respective wafers to align with each other, and because of the extreme tolerances that would be required, they generally will not align, but instead will be offset from each other as shown in the figure. There will also be some vertical separation 106 between the two wafers, due to their surface roughness.

A gasket (not shown) set between the two wafers confines the pre-existing aqueous phase B. This aqueous phase maintains a continuous ionic path between the gold detector electrode D at the bottom of wafer 102 and the silver preconcentrator electrode C at the bottom of wafer 101.

Figure 11A:
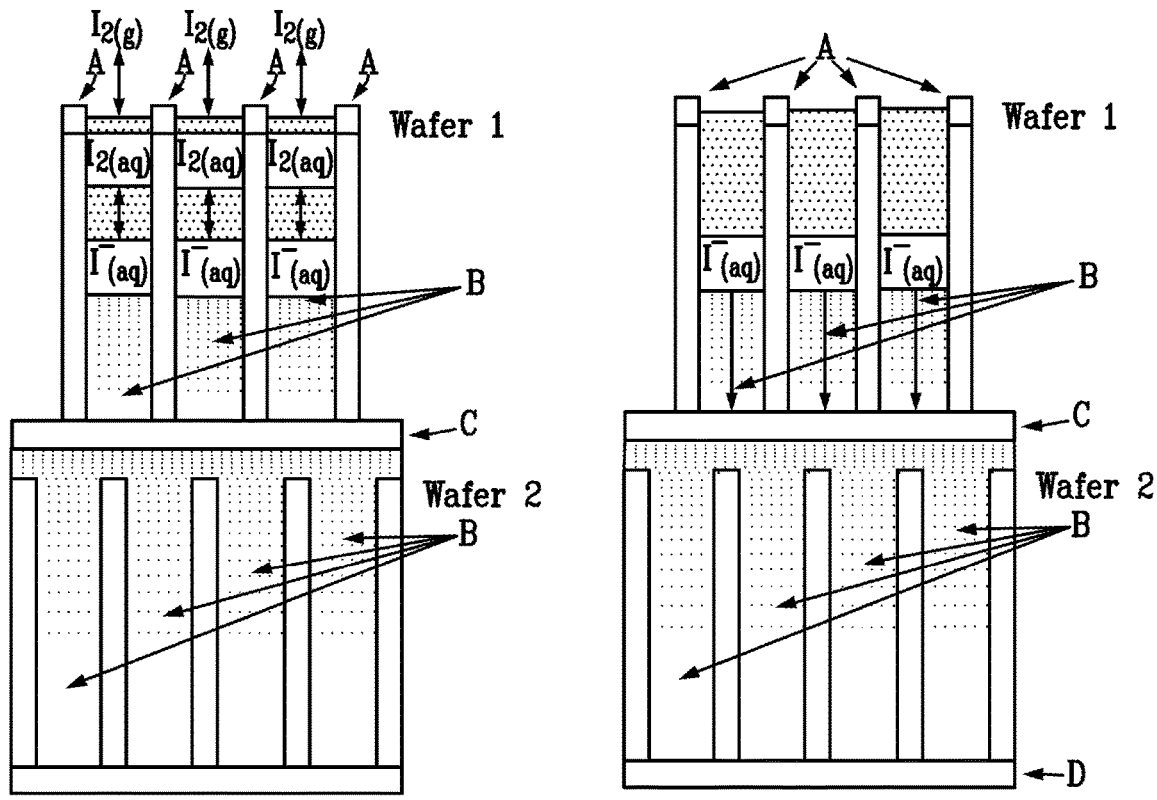
FIGS. 11A and 11B illustrate four stages in the use of the sensor of FIG. 10 for detecting iodide.

The upper wafer 101 is designed to operate as the accumulation cell. Iodine gas enters the wafer at location a, the gas/aqueous interface of the sensor, and is hydrolyzed to iodine as an equilibrium product of the reaction (Step 1 of FIG. 11A). In the accumulation call, the iodide is electrochemically stored in the silver electrode (identified as material C) as silver iodide by the aforementioned anodic reaction (Step 2 of the figure). The anodic reaction is enabled by a platinum electrode A that serves as the as the cell's auxiliary and pseudoreference electrode. The accumulation can be controlled so that, for example, it proceeds for a set amount of time, or until a set amount of charge has been exchanged, or to some other endpoint that may, e.g., be monitored autonomously.

Figure 11B:
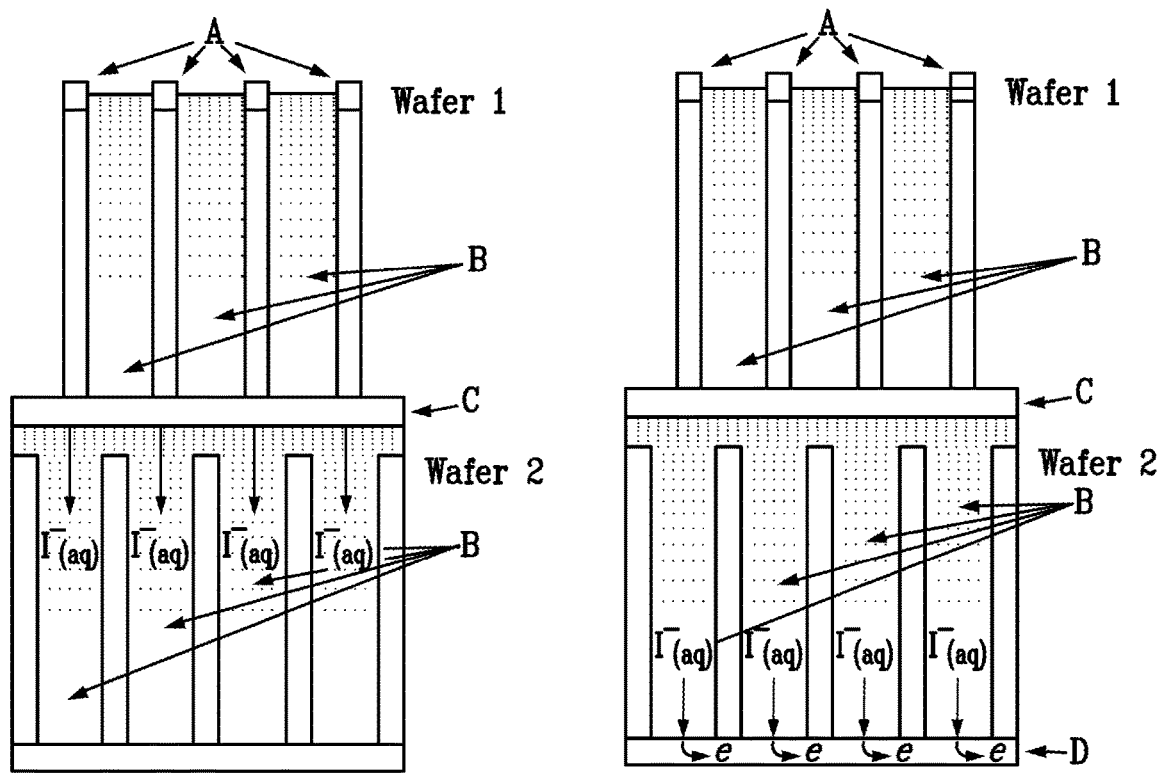

After the accumulation period, a different electrochemical cell is engaged to release the concentrated iodide into the aqueous volume that contacts the detector electrode D (Step 3 of FIG. 11B). For that purpose, the silver preconcentrator electrode is biased with an electronegative potential sufficient to accomplish the cathodic reaction releasing the iodide. The detector electrode serves a dual role as both auxiliary and pseudoreference electrode for this electrochemical step. Because the detector electrode is completing the electrochemical circuit, an electric field is established that tends to direct the released iodide toward the detector electrode.

In Step 4 as indicated in the figure, a third electrochemical cell configuration detects the iodide in proximity to the detector electrode D. The detector electrode is biased sufficiently electropositive to enable anodic reactions with iodide, such as the reactions

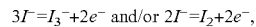
$$3I^-=I_3^-+2e^- \text{ and/or } 2I^-=I_2+2e^-,$$

that transfer electrons whose detection, via current sensing, signifies the iodide concentration. The platinum electrode A serves as the required auxiliary and pseudoreference electrode to complete the electrochemical cell.

It should also be noted that by reversing this sequence of steps, iodide can be discharged from the sensor environment to reset the cell.

Figure 12:
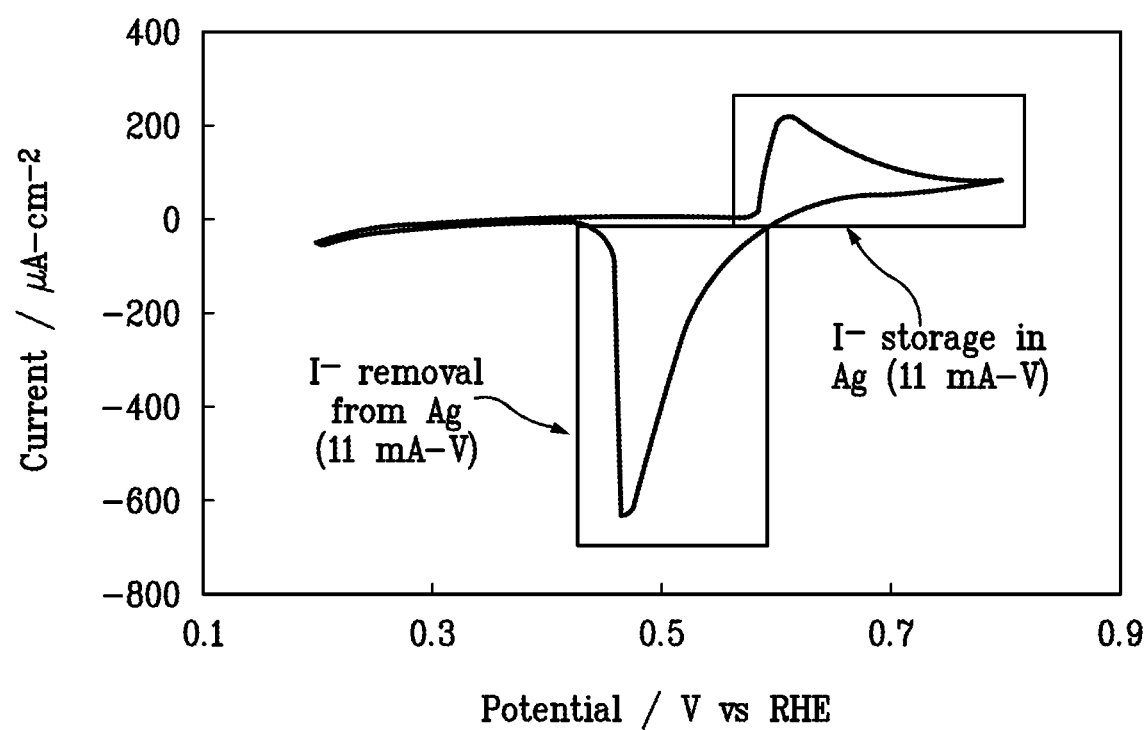
FIG. 12 is a cyclic voltammogram that provides experimental evidence for the reversible charging and discharging of silver with iodine.

Experimental evidence for the reversible charging and discharging of silver with iodine is shown in FIG. 12. To produce the displayed voltammogram, 30 cycles of reversible charging and discharging of iodide were performed during cyclic voltammetry conducted at 20 mV/s in a silver electrode through an electrolyte of pH 9 phosphate buffer. The efficiency of the cycling is near 100%.

Figure 13:
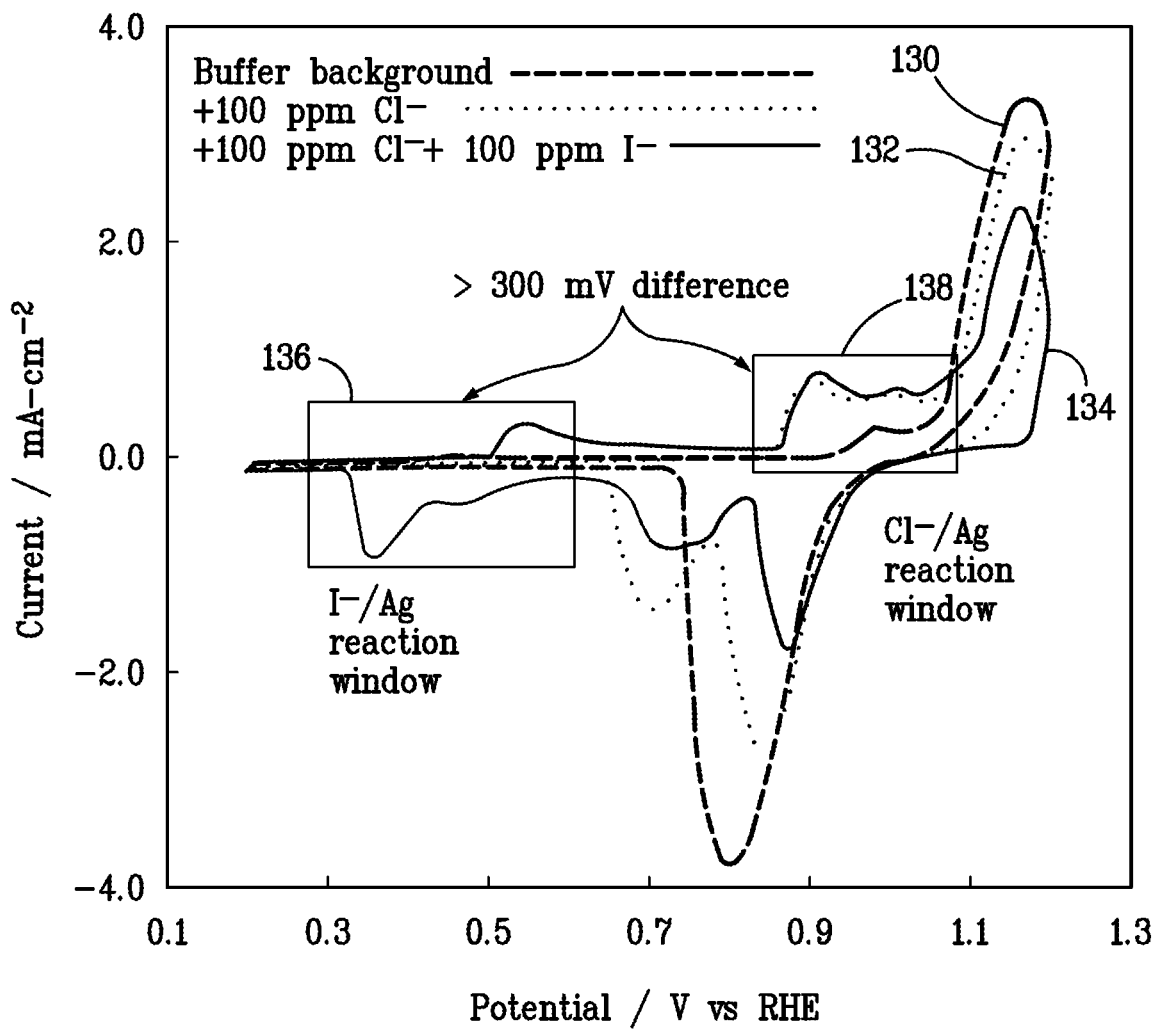
FIG. 13 is a superposed set of three cyclic voltammograms demonstrating the selective oxidation at a silver electrode of iodide and chloride, respectively, at different potentials.

Our experiments provided evidence of selective charging of halide ions in silver that discriminated between iodide and chloride. The evidence is shown in FIG. 13, where three voltammograms are displayed: A background voltammogram 130 taken on a buffered solution without dissolved chloride or iodide, a voltammogram 132 taken on a solution of 100 ppm chloride, and a voltammogram 134 taken on a solution of 100 ppm chloride and 100 ppm iodide. The figure shows that the oxidation of iodide to form AgI may be performed at potentials 136 near 0.5 V (vs. RHE), which is roughly 300 mV lower than the potential 138 at which chloride is oxidized to form AgCl. This suggests silver can be used to selectively extract iodide from the electrolyte when it serves either as a selective preconcentrator or as a working electrode.

As noted above, the accumulation of iodide may also be done by the hydrolysis of iodine gas in the aqueous electrolyte of the sensor. The electrolyte can serve as a sink, allowing the hydrolyzed species of iodine gas to accumulate in the sensor. Turning back to FIG. 9, it will be seen there that when iodine gas is flowed through a pH 9 buffer solution, there is a linear accumulation of iodide ions in the buffer as a function of the production of exposure time and the concentration of iodine in the gas flow. The measured saturation point of iodide ions accumulated in the pH 9 buffer from this accumulation method is greater than 400 ppm.

Further Embodiments 2: Use of Absorption Beds

In example embodiments, an absorption bed in which preconcentrator material is disposed as, e.g., a film or particulate layer may operate as a preconcentrator for gas-phase environments. Many suitable preconcentrator materials are known, including metal-organic-framework materials (MOFs), zeolites, and activated carbons.

MOF materials may be of particular interest in this regard. They are chemically, mechanically, and radiologically stable microporous crystalline structures that combine the connectivity of metal centers with the bridging ability of organic ligands. By judiciously choosing the metal and the linker (i.e., the organic ligand that attaches to the metal center), structures can be designed and synthesized to have tailored functionality, pore sizes, and pore shapes.

The specific surface area of a typical MOF is greater than 1000 m$^2$/g, which exceeds typical values for zeolites by an order of magnitude. This makes MOFs highly attractive candidate materials for preconcentrating gas molecules. For chemical selectivity, the structure of the MOF can be tuned for maximum binding of the target molecule to either the metal center or the core linker.

Iodine gas sorption by MOFs has been demonstrated in both single and mixed-gas systems. Specific MOFs, such as ZIF-8 and HKUST-1, are known to have high selectivity for iodine. ZIF-8 has a small pore opening of about 0.34 nm, can reportedly capture 125% of its weight in iodine, and is stable in both air and water. Its ability to selectively capture iodine is attributable to the combined effects of pore size and binding by the organic ligand. HKUST-1 has a larger pore channel of about 1 nm. It can separate iodine from water and can capture 175% of its weight in iodine. The ability of HKUST-1 to selectively capture iodine is attributable to strong bonding to the copper atoms that constitute the metal centers of the MOF structure.

Figure 14:
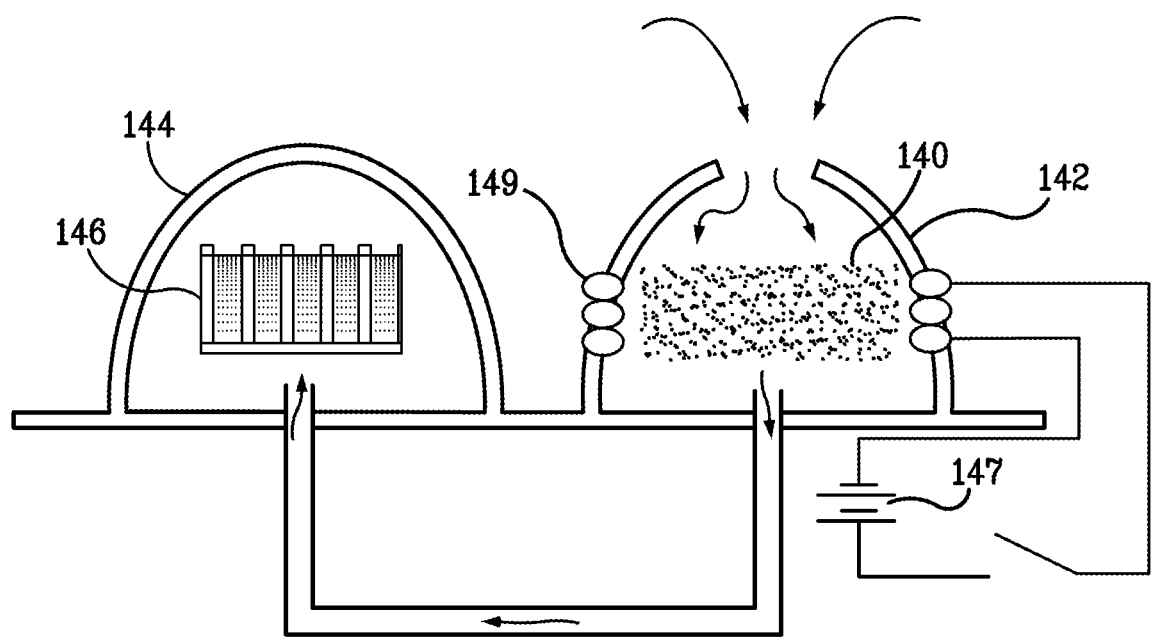
FIG. 14 is a notional diagram showing the use of an absorption bed of preconcentrator material in combination with a sensor of the kind described here.

The absorption bed can take any of various possible forms. For example, it can be added as a film or coating of preconcentrator material held in proximity to the MEA surface. In other approaches, it can be added as a powder bed in a separate chamber. FIG. 14 is a notional diagram including a schematic representation of an absorption bed 140 in use as a preconcentrator material. In the figure, absorption bed 140 is shown as a powder bed in a chamber 142 that is separate from the chamber 144 containing the sensor 146.

Any of various processes may be useful for releasing the sorbed gas from the absorption bed into the MEA sensor. The specific choice may depend on the target analyte gas and the type of preconcentrator material used. Some suitable processes include electrochemical stimulus, pressure-driven release, and temperature-driven release. Each of these mechanisms has advantages and disadvantages depending on the material combinations.

For example, electrochemical stimuli are ineffective for releasing iodine gas from either of the MOFs known as ZIF-8 and HKUST-1. However, thermal stimulus by heating to temperatures of about 100° C. may work well. Such a thermal stimulus can be created using a heater to raise the temperature of the MOF bed after it has accumulated target species over a period of time. An example heater suitable for that purpose is a microheater fabricated onto the backside of the substrate or container of the MOF bed. Operation of the heater would release the captured analyte gas for dissolution into the MEA microwells, or for absorption into a secondary preconcentrator. Release from the secondary preconcentrator is effectuated by, e.g., an electrochemical stimulus.

As indicated in FIG. 14, the thermal stimulus can be provided by passing electric current from a battery 147 through a resistive heating element 149. However, it may be possible, in the alternative, to heat the absorption bed without using a fabricated heater. One example would be to utilize solar heating of a separate compartment containing only the absorption bed. That compartment could be coated with a solar radiation-absorbing material. An example would be an ultra-black material containing, e.g., vertically-aligned arrays of carbon microtubes, as is known in the art.

An actively or passively heated absorption bed is preferably housed in a separate chamber from the MEA sensor for thermal isolation, so that evaporative loss of electrolyte from the microwells due to heating is minimized. Below, we refer to such a chamber as an absorption chamber.

In an example sequence of operational steps, the absorption chamber is exposed to the atmosphere being tested, so that the absorption bed can absorb the sought-for gaseous species over a period of time. The absorption bed is then heated, e.g. passively or by a microheater, so that a flow of released analyte gas will enter a second chamber containing the MEA array. A secondary preconcentrator coating may be in place within the MEA chamber, possibly at or near the open mouths of the pores of the MEA. The MEA chamber is at a lower temperature than the absorption chamber, which may be facilitated by connecting the two chambers with a thermally insulating material. The MEA chamber may also have its external walls coating with a light-reflecting material to minimize ambient heating.

We claim:

1. An electrochemical sensor, comprising:
   a plurality of working nanoelectrodes arranged in an array and interconnected in parallel;
   a counter electrode structure; and
   a nanoporous body, wherein:
     the counter electrode structure or a further electrode structure is configured to serve as a reference electrode;
     at least a portion of the nanoporous body is configured to be exposed to a gaseous environment;
     at least a portion of the nanoporous body is configured to contain an electrolyte, a boundary between the gaseous environment and the electrolyte being situated within or adjacent to the nanoporous body;
     the working nanoelectrodes are configured to be electrochemically coupled to the counter electrode structure through the electrolyte; and
     the nanoporous body is a layer of anodized aluminum oxide (AAO) perforated with an array of mutually parallel nanopores extending from a front face to a back face thereof.

2. The electrochemical sensor of claim 1, wherein the working nanoelectrodes are situated wholly or partially within nanopores of the nanoporous body.

3. The electrochemical sensor of claim 1,
   wherein the nanoporous body has a front face configured to be exposed to the gaseous environment, and
   wherein the nanoporous body has a back face configured to be exposed to an enclosed fill volume for the electrolyte.

4. The electrochemical sensor of claim 1,
   wherein the nanoporous body has a front face configured to be exposed to the gaseous environment, and
   wherein the nanoporous body is configured to electrochemically couple the working nanoelectrodes to the counter electrode structure through electrolyte contained within nanopores of the nanoporous body.

5. The electrochemical sensor of claim 1, further comprising a preconcentrator layer configured to release a preconcentrated analyte onto a path between the gaseous environment and the working nanoelectrodes.

6. The electrochemical sensor of claim 5, wherein the preconcentrator layer is configured to be outside of the electrolyte.

7. The electrochemical sensor of claim 5, wherein the preconcentrator layer is configured to be within the electrolyte.

8. The electrochemical sensor of claim 5, wherein the preconcentrator layer comprises a porous metal selected to be electrochemically reactive to an analyte that is to be detected.

9. The electrochemical sensor of claim 5, wherein the preconcentrator layer comprises a preconcentrator material chosen to capture a desired analyte from the gaseous environment and to preconcentrate the desired analyte.

10. The electrochemical sensor of claim 5, further comprising an electric heater thermally connected to the preconcentrator layer, whereby energizing the electric heater releases analyte from the preconcentrator layer.

11. The electrochemical sensor of claim 5, further comprising a pressurizer or depressurizer in fluidic contact with an atmosphere surrounding the preconcentrator layer, whereby activating the pressurizer or depressurizer releases analyte from the preconcentrator layer.

12. The electrochemical sensor of claim 5, wherein:
the preconcentrator layer comprises a porous metal electrode; and
said porous metal electrode is configured to drive concentration of an analyte upon energizing by a first relative voltage and is configured to drive release of the analyte upon energizing by a second relative voltage.

13. The electrochemical sensor of claim 12,
wherein the first relative voltage is between the porous metal electrode and the counter electrode structure, and
wherein the second relative voltage is between the porous metal electrode and the working nanoelectrodes.

14. A sensing method, comprising:
admitting a gas sample to a liquid electrolyte maintained by nanopores of a nanoporous substrate, the nanoporous substrate including a layer of anodized aluminum oxide (AAO) perforated with an array of mutually parallel nanopores extending from a front face to a back face thereof;
applying a voltage to the liquid electrolyte; and
observing an electrical response to the applied voltage, thereby to detect electrochemical evidence of an analyte within the liquid electrolyte.

15. The sensing method of claim 14, wherein the liquid electrolyte is a product of capillary condensation within the nanopores from an ambient gaseous atmosphere.

16. The sensing method of claim 14,
wherein analyte within the gas sample is captured and preconcentrated by a preconcentrator material, and
the sensing method further comprises releasing the preconcentrated analyte from the preconcentrator material into the liquid electrolyte.

17. The sensing method of claim 16, wherein the releasing of the preconcentrated analyte is performed by heating the preconcentrator material or by causing a change in pressure on the preconcentrator material.

18. The sensing method of claim 16, wherein the analyte within the gas sample is captured in the liquid phase and preconcentrated by a chemical or electrochemical reaction with the preconcentrator material.

19. The sensing method of claim 16, wherein the releasing of the preconcentrated analyte from the preconcentrator material is performed by driving an electrochemical reaction.

20. The sensing method of claim 16, wherein:
the analyte within the gas sample is captured and preconcentrated by at least a first and a second preconcentrator material;
heat or pressure is used to release the preconcentrated analyte from the first preconcentrator material so that it then interacts with the second preconcentrator material; and
an electrochemical reaction is used to release the preconcentrated analyte from the second preconcentrator material into the liquid electrolyte.

* * * * *